(12) United States Patent
Jarrett et al.

(10) Patent No.: US 6,380,157 B1
(45) Date of Patent: Apr. 30, 2002

(54) METHOD OF TREATMENT USING PAPILLOMAVIRUS L2 PROTEIN

(75) Inventors: William Fleming Hoggan Jarrett; Maria Saveria Campo; Kenneth Thomas Smith, all of Glasgow (GB)

(73) Assignee: Cancer Research Campaign Technology Limited, London (GB)

(*) Notice: Subject to any disclaimer, the term of this patent is extended or adjusted under 35 U.S.C. 154(b) by 0 days.

(21) Appl. No.: 08/484,791

(22) Filed: Jun. 7, 1995

Related U.S. Application Data

(63) Continuation of application No. 08/170,185, filed as application No. PCT/GB92/01092 on Jun. 17, 1992, now abandoned.

(30) Foreign Application Priority Data

Jun. 26, 1991 (GB) ............................................. 9113809

(51) Int. Cl.$^7$ ......................... A61K 38/04; A61K 38/16

(52) U.S. Cl. ................... 514/12; 424/192.1; 424/186.1; 514/2; 514/8; 514/13; 514/14; 514/15; 514/16; 514/17; 514/18; 514/19

(58) Field of Search .............................. 435/69.7, 69.1, 435/172.3; 514/12, 2, 8, 13, 14–19; 530/403; 424/192.1, 156.1, 184.1

(56) References Cited

U.S. PATENT DOCUMENTS 4,777,239 A   10/1988   Schoolnik et al. .......... 530/326
5,591,574 A   1/1997    Orth et al. ..................... 435/5

FOREIGN PATENT DOCUMENTS

EP          A 0133123      2/1985

OTHER PUBLICATIONS

Lancaster et al. Human papillomavirus infection and neoplasia: speculations for the future. Dermatologic Clinics. vol. 9, No. 2, pp. 371–376, Apr. 1991.
Potter et al. Bovine papillomavirus type 2 late region DNA encoding structural proteins L1 and L2, complete cds. GenBank Accession No. M24326, Sep. 15, 1989.
Pilacinski et al. Cloning and expression in *Escherichia coli* of the bovine papillomavirus L1 and L2 open reading frames. Bio/Technology. vol. 2, pp. 356–360, Apr. 1984.
Pilacinski et al. Immunization against bovine papillomavirus infection. CIBA Foundation Symposium. vol. 120, Abstract, 1986.
Rippe et al. Identification and characterization of the BPV–2 L2 protein. Virology. vol. 171, No. 1, pp. 298–301, Jul. 1989.*

Strike et al. Expression in *Escherichia coli* of seven DNA fragments comprising the complete L1 and L2 open reading frames of human papillomavirus type 6b and localization of the 'common antigen' region. Journal of General Virology, vol. 70, Pt 3, pages., Mar. 1989.*
Tomita et al. Expression of the humna papillomavirus type 6b L2 open reading frame in *Escherichia coli*: L2– –galactosidase fusion proteins and their antigenic properties. Virology. vol. 158, pp. 8–14, 1987.*
Thompson et al. Expression of human papillomavirus type 6 E1, E2, L1 and L2 open reading frames in *Escherichia coli*. Gene. vol. 56, No. 2–3, pp. 289–295, 1987.*
Christensen, et al., "The Open Reading Frame L2 of Cottontail Papillomavirus Contains Antibody–Inducing Neutralizing Epitopes," *Biological Abstracts*, 91(10):516, Abstract No. 107549.
Christensen, et al., "The Open Reading Frame L2 of Cottontail, Rabbit Papillomavirus Contains Antibody–Inducing Neutralizing Epitopes," *Virology*, 181(2):572–579 (1991).
Smith, et al., "Single Step Purification of Polypeptides Expressed in *Escherichia Coli* as Fusions with Glutathione S–Transferase," *Gene*, 67:31–40 (1988).
Meneguzzi et al., "Vaccine Recombinants Expressing Early Bovine Papilloam Virus (BPV1) Proteins: Retardation of BPV1 Tumor Development," *Vaccine*, 8(3):199–204 (1990).
Potter, et al., "Nucleotide Sequence of Bovine Papillomavirus Type 2 Late Region," *J. Gen. Virol.*, 66(1):187–193 (1985).
Patel, et al., "The Nucleotide Sequence and Genome Organization of Bovine Papillomavirus Type 4," *J. Gen. Virol.*, 68(8):2117–2128 (1987).
Jarrett, et al., "Studies on Vaccination Against Papillomaviruses: Prophylactic and Therapeutic Vaccination with Recombinant Structural Proteins," *Virology*, 184(1):33–42 (1991).
Evans, et al., "Antitumor Immunity in the Shope Papilloma–Carcinoma Complex of Rabbits. I. Papilloma Regression Induced by Homologous and Autologous Tissue Vaccines," *J. Nat. Cancer Inst.*, 29:277–285 (1962).
Abcarian, et al., "The Effectiveness of Immunotherapy in the Treatment of Anal Condyloma Acuminatum," *J. Surg. Res.*, 22:231–236 (1977).
Yurdakok, et al., "Vaccine Therapy of Warts in Children," *Turkish Journal of Pediatrics*, 27:87–94 (1985).
Malison, et al., "Autogenous Vaccine Therapy for Condyloma Acumination—a Double–Blind Controlled Study," *Brit. J. Venereal Dis.*, 58:62–65 (1982).

(List continued on next page.)

Primary Examiner—Michael Pak
(74) Attorney, Agent, or Firm—Klarquist Sparkman, LLP (57) ABSTRACT

The L2 protein of papillomavirus (particularly BPV-2 and BPV-4) has been cloned as a fusion protein with beta-galactosidase and GST; both as the whole protein and as fragments. Vaccination of calves is found to have both a prophylactic effect in tumour prevention and a therapeutic effect in tumour regression.

13 Claims, 4 Drawing Sheets

OTHER PUBLICATIONS

Kreider, et al., "The Shope Papilloma–Carcinoma Complex of Rabbits: A Model System of Neoplastic Progression and Spontaneous Regression," *Adv. Cancer Res.*, 35:81–109 (1981).

Schreier, et al., "Prospects for Human Papillomavirus Vaccines and Immunotherapies," *J. Nat'l. Cancer Inst.*, 80:896–899 (1988).

Lin et al., "Effective Vaccination Against Papilloma Development by Immunization with L1 or L2 Structural Protein of Cottontail Rabbit Papillomavirus," *Virology*, 187:612–619 (1992).

Lancaster, et al., "Human Papillomavirus Infection & Neoplasia," *Dermatologic Clinics*. 9(2):371–376 (1991).

* cited by examiner

SEQUENCE LISTING

```
(1) GENERAL INFORMATION:

(iii) NUMBER OF SEQUENCES: 2

(2) INFORMATION FOR SEQ ID NO:1:

(i) SEQUENCE CHARACTERISTICS:
           (A) LENGTH: 2910 base pairs
           (B) TYPE: nucleic acid
           (C) STRANDEDNESS: double
           (D) TOPOLOGY: linear (ii) MOLECULE TYPE: DNA (genomic)

(ix) FEATURE:
           (A) NAME/KEY: CDS
           (B) LOCATION: 1..1401

(ix) FEATURE:
```

(A) NAME/KEY: CDS
        (B) LOCATION: 1417..2907

(xi) SEQUENCE DESCRIPTION: SEQ ID NO:1:

```
ATG AGT GCA CGA AAA AGG GTG AAA CGT GCA AAT GTC TAT GAC CTG TAC        48
Met Ser Ala Arg Lys Arg Val Lys Arg Ala Asn Val Tyr Asp Leu Tyr
1               5                   10                  15

AGG ACT TGC AAG CAA GCG GGC ACC TGT CCA CCA GAT GTG ATA CCT AAG        96
Arg Thr Cys Lys Gln Ala Gly Thr Cys Pro Pro Asp Val Ile Pro Lys
            20                  25                  30

GTA GAA GGT GAC ACT ATA GCA GAC AAG ATT TTA AAA TTA GGA GGC CTT       144
Val Glu Gly Asp Thr Ile Ala Asp Lys Ile Leu Lys Leu Gly Gly Leu
        35                  40                  45

GCA ATT TAT CTG GGG GGC CTA GCT ATT GGA ACA TGG TCT ACA GGA AGA       192
Ala Ile Tyr Leu Gly Gly Leu Ala Ile Gly Thr Trp Ser Thr Gly Arg
    50                  55                  60

GTG GCT GCA GGA GGA TCA CCT AGG TAT GTA CCC TTA AGA ACC TCT GGA       240
Val Ala Ala Gly Gly Ser Pro Arg Tyr Val Pro Leu Arg Thr Ser Gly
65                  70                  75                  80

TCC ACT ACA AGC CTG GCA TCT GTA GGA TCC AGG GCT GGT GCA GCC ACT       288
Ser Thr Thr Ser Leu Ala Ser Val Gly Ser Arg Ala Gly Ala Ala Thr
                85                  90                  95

GGC ACT CGC AGC AGC ATC ACA GGA ATC CCC CTT GAC ACC CTA GAA ACT       336
Gly Thr Arg Ser Ser Ile Thr Gly Ile Pro Leu Asp Thr Leu Glu Thr
            100                 105                 110

ATT GGG GCT CTT CGT CCT GGA GCT TAT GAA GAC ACT GTG CTC CCA GAG       384
Ile Gly Ala Leu Arg Pro Gly Ala Tyr Glu Asp Thr Val Leu Pro Glu
        115                 120                 125

GCC CCT GCT ATT GTC ACC CCT GAT GCT GTA CCT GCG GAC ACA GGG ATA       432
Ala Pro Ala Ile Val Thr Pro Asp Ala Val Pro Ala Asp Thr Gly Ile
    130                 135                 140

GAT GGC CTT TCT ATA GGC ACT GAC TCT TCC ACT GAA ACT TTA ATC ACA       480
Asp Gly Leu Ser Ile Gly Thr Asp Ser Ser Thr Glu Thr Leu Ile Thr
145                 150                 155                 160

TTG TTA GAG CCT GAG GGT CCT GAA GAC GTG GCA GTC TTA GAG CTG CAA       528
Leu Leu Glu Pro Glu Gly Pro Glu Asp Val Ala Val Leu Glu Leu Gln
                165                 170                 175

CCT CTA GAC CAT GCA AAT TGG CAA GTT AGC AAT GCT GTT CAT CAG GGC       576
Pro Leu Asp His Ala Asn Trp Gln Val Ser Asn Ala Val His Gln Gly
            180                 185                 190

TCT GCA TAC CAC GCC CCT CTG CAG CTG CAG TCC TCC ATT GCA GAA ACA       624
Ser Ala Tyr His Ala Pro Leu Gln Leu Gln Ser Ser Ile Ala Glu Thr
        195                 200                 205

TCT GGA CTA GAA AAT ATT TTT GTA GGA GGG GCT GGG TTA GGG GAT ACA       672
Ser Gly Leu Glu Asn Ile Phe Val Gly Gly Ala Gly Leu Gly Asp Thr
    210                 215                 220

GGC GGA GAG AAC ATA GAG CTC ACA TTT TTT GGT TCC CCA CGC ACA AGT       720
Gly Gly Glu Asn Ile Glu Leu Thr Phe Phe Gly Ser Pro Arg Thr Ser
225                 230                 235                 240

ACC CCC CGT AAC CTG CCT CAA ACT GCA CGG GGC ATC TTG AAC TGG TTT       768
Thr Pro Arg Asn Leu Pro Gln Thr Ala Arg Gly Ile Leu Asn Trp Phe
                245                 250                 255

AGC AAA AGA TAC TAC ACA CAA ATA CCC ACA GAA GAC CCT GAT GTC TTT       816
Ser Lys Arg Tyr Tyr Thr Gln Ile Pro Thr Glu Asp Pro Asp Val Phe
            260                 265                 270

TCA TCA CAG ACA TTT TCA AAC CCA GTG TAT GAT CCT GAG CCT GCA GTG       864
Ser Ser Gln Thr Phe Ser Asn Pro Val Tyr Asp Pro Glu Pro Ala Val
        275                 280                 285

CTA AAA GGT CCC AGT GGC CGT GTG GGG CTA AGC CAA GTG TAT AGG CCT       912
Leu Lys Gly Pro Ser Gly Arg Val Gly Leu Ser Gln Val Tyr Arg Pro
```

```
              290                 295                 300
GAC TAT ATT GAA ACA CGG GGT GGG GGT CAG GTG GGC CCA CAG CTG CAT        960
Asp Tyr Ile Glu Thr Arg Gly Gly Gly Gln Val Gly Pro Gln Leu His
305                 310                 315                 320

GTC AGG TAC TCC TTA AGC ACT ATC ACA GAA GAT GTG GAA GCC ATA CCT       1008
Val Arg Tyr Ser Leu Ser Thr Ile Thr Glu Asp Val Glu Ala Ile Pro
                    325                 330                 335

ATA GCA GTT GAT GAA GAC ACA CAA GGG CTA GCA TTT CTT CCT TTA CAT      1056
Ile Ala Val Asp Glu Asp Thr Gln Gly Leu Ala Phe Leu Pro Leu His
                340                 345                 350

GAA GAA CCA GGG GAC TTT GAA GAA ATT GAG CTA GAT GAT TTA GGT GAA      1104
Glu Glu Pro Gly Asp Phe Glu Glu Ile Glu Leu Asp Asp Leu Gly Glu
            355                 360                 365

GAG CAC GCC TTG CTC CCC AAG TCA TCT ACT GCA CCT ATT GGT AGT GGA      1152
Glu His Ala Leu Leu Pro Lys Ser Ser Thr Ala Pro Ile Gly Ser Gly
370                 375                 380

GTT CGT AGG GCG CTC ATT CCA GGT CAA GGC TTC AGT GCA ACA CGG CCC      1200
Val Arg Arg Ala Leu Ile Pro Gly Gln Gly Phe Ser Ala Thr Arg Pro
385                 390                 395                 400

ACA GGT GTG GTA ACC TAT GGC TCA CCT GAC ATG TAC CCT GCT AGC CCT      1248
Thr Gly Val Val Thr Tyr Gly Ser Pro Asp Met Tyr Pro Ala Ser Pro
                    405                 410                 415

GTT GGC CCT GAC TCG ACA TCC CCT AGC CTA GTT ATT GAT GAC AAC ACA      1296
Val Gly Pro Asp Ser Thr Ser Pro Ser Leu Val Ile Asp Asp Asn Thr
                420                 425                 430

ACA ACA CCA ATA ATC ATT ATT GAT GGC CAC ACA GTG GAT CTG TAT AGC      1344
Thr Thr Pro Ile Ile Ile Ile Asp Gly His Thr Val Asp Leu Tyr Ser
            435                 440                 445

AAT AAC TAT AGC TTG CAT CCC TCC TTG TTG AGG AAA AGA AAA AAA CGG      1392
Asn Asn Tyr Ser Leu His Pro Ser Leu Leu Arg Lys Arg Lys Lys Arg
450                 455                 460

AAA CAT GCC TAATTTTTTT TGCAG ATG GCG TTG TGG CAA CAA GGC CAG AAG     1443
Lys His Ala                 Met Ala Leu Trp Gln Gln Gly Gln Lys
465                                         470                 475

CTG TAT CTC CCT CCA ACC CCT GTA AGC AAG GTG CTA TGC AGT GAA ACC      1491
Leu Tyr Leu Pro Pro Thr Pro Val Ser Lys Val Leu Cys Ser Glu Thr
                    480                 485                 490

TAT GTG CAA AGA AAA AGC ATA TTT TAT CAT GCA GAA ACG GAA CGC CTG      1539
Tyr Val Gln Arg Lys Ser Ile Phe Tyr His Ala Glu Thr Glu Arg Leu
                495                 500                 505

TTA ACT GTA GGA CAT CCA TAC TAC CAA GTC ACT GTG GGG GAC AAA ACT      1587
Leu Thr Val Gly His Pro Tyr Tyr Gln Val Thr Val Gly Asp Lys Thr
            510                 515                 520

GTT CCC AAA GTG TCT GCT AAT CAA TTT AGA GTT TTT AAA ATA CAG CTC      1635
Val Pro Lys Val Ser Ala Asn Gln Phe Arg Val Phe Lys Ile Gln Leu
525                 530                 535                 540

CCC GAT CCC AAT CAG TTT GCA TTG CCT GAT AGG ACT GTG CAC AAT CCA      1683
Pro Asp Pro Asn Gln Phe Ala Leu Pro Asp Arg Thr Val His Asn Pro
                    545                 550                 555

AGC AAG GAG CGC CTG GTG TGG GCT GTA ATA GGG GTT CAA GTG TCT CGT      1731
Ser Lys Glu Arg Leu Val Trp Ala Val Ile Gly Val Gln Val Ser Arg
                560                 565                 570

GGC CAA CCA CTA GGA GGC ACA GTT ACT GGG CAC CCC ACT TTT AAT GCT      1779
Gly Gln Pro Leu Gly Gly Thr Val Thr Gly His Pro Thr Phe Asn Ala
            575                 580                 585

CTG CTT GAT GCA GAA AAT GTT AAT AGA AAA GTT ACT GCA CAA ACA ACA      1827
Leu Leu Asp Ala Glu Asn Val Asn Arg Lys Val Thr Ala Gln Thr Thr
590                 595                 600

GAT GAC AGG AAG CAA ACA GGA TTA GAT GCT AAG CAA CAA CAG ATT CTG      1875
```

-continued

```
Asp Asp Arg Lys Gln Thr Gly Leu Asp Ala Lys Gln Gln Ile Leu
605                 610                 615                 620

TTG CTG GGC TGT ACC CCT GCA GAA GGG GAA TAT TGG ACC ACA GCC CGT    1923
Leu Leu Gly Cys Thr Pro Ala Glu Gly Glu Tyr Trp Thr Thr Ala Arg
                    625                 630                 635

CCA TGT GTT ACT GAT AGA ATA GAA AAT GTT GCG TGT CCT CCT TTA GAA    1971
Pro Cys Val Thr Asp Arg Ile Glu Asn Val Ala Cys Pro Pro Leu Glu
                640                 645                 650

TTA AAG AAC AAA CAC ATA GAA GAT GGA GAC ATG ATG GAA ATA GGG TTT    2019
Leu Lys Asn Lys His Ile Glu Asp Gly Asp Met Met Glu Ile Gly Phe
            655                 660                 665

GGT GCT GCT GAC TTT AAA ACA CTA AAT GCC AGT AAA TCA GAT CTA CCT    2067
Gly Ala Ala Asp Phe Lys Thr Leu Asn Ala Ser Lys Ser Asp Leu Pro
        670                 675                 680

TTT GAC ATT CAA AAT GAA ATA TGC CTG TAT CCA GAC TAC CTC AAA ATG    2115
Phe Asp Ile Gln Asn Glu Ile Cys Leu Tyr Pro Asp Tyr Leu Lys Met
685                 690                 695                 700

GCT GAA GAT GCT GCT GGA AAC AGT ATG TTC TTC TTT GCA AGA AAA GAA    2163
Ala Glu Asp Ala Ala Gly Asn Ser Met Phe Phe Phe Ala Arg Lys Glu
                    705                 710                 715

CAA GTG TAT GTA AGG CAT ATA TGG ACT CGG GGG GGC TCT GAA AAA GAA    2211
Gln Val Tyr Val Arg His Ile Trp Thr Arg Gly Gly Ser Glu Lys Glu
                720                 725                 730

GCA CCC AGT AAA GAC TTC TAC CTC AAA AAT GGT AGA GGT GAA GAA ACT    2259
Ala Pro Ser Lys Asp Phe Tyr Leu Lys Asn Gly Arg Gly Glu Glu Thr
            735                 740                 745

CTG AAA ATA CCT AGT GTG CAC TTT GGC AGT CCC AGT GGA TCC TTG GTG    2307
Leu Lys Ile Pro Ser Val His Phe Gly Ser Pro Ser Gly Ser Leu Val
        750                 755                 760

TCC ACT GAT AAT CAA ATA TTT AAC AGG CCT TAT TGG CTA TTC AGG GCT    2355
Ser Thr Asp Asn Gln Ile Phe Asn Arg Pro Tyr Trp Leu Phe Arg Ala
765                 770                 775                 780

CAG GGC ATG AAC AAT GGG ATT GCA TGG GAT AAT TTA TTA TTT TTA ACT    2403
Gln Gly Met Asn Asn Gly Ile Ala Trp Asp Asn Leu Leu Phe Leu Thr
                    785                 790                 795

GTA GGG GAT AAC ACA CGG GGA ACT AAC CTT AGT ATT AGT GTA GCT GCA    2451
Val Gly Asp Asn Thr Arg Gly Thr Asn Leu Ser Ile Ser Val Ala Ala
                800                 805                 810

GAT GGA AAC GCA TTG TCA GAG TAT GAT ACT GGC AAA TTT AAC CTA TAC    2499
Asp Gly Asn Ala Leu Ser Glu Tyr Asp Thr Gly Lys Phe Asn Leu Tyr
            815                 820                 825

CAT AGG CAT ATG GAA GAA TAT AAG CTA GCA TTT ATA TTG GAG CTG GTC    2547
His Arg His Met Glu Glu Tyr Lys Leu Ala Phe Ile Leu Glu Leu Val
        830                 835                 840

TCT GTT GAG ATT ACT GCA CAA ACA GTG TCA CAT CTG CAA GGA CTG ATG    2595
Ser Val Glu Ile Thr Ala Gln Thr Val Ser His Leu Gln Gly Leu Met
845                 850                 855                 860

CCC TCT GTG CTA CAA AAC TGG GAA ATC GGG GTG CAA CCT CCT GCT TCT    2643
Pro Ser Val Leu Gln Asn Trp Glu Ile Gly Val Gln Pro Pro Ala Ser
                    865                 870                 875

TCT ATT TTA GAA GAT ACC TAT AGG TAC ATA GAG TCT CCT GCA ACT AAA    2691
Ser Ile Leu Glu Asp Thr Tyr Arg Tyr Ile Glu Ser Pro Ala Thr Lys
                880                 885                 890

TGT GCA AGT AAT GTT ATA CCA CCC AAA GAA GAC CCT TAT GCA GGC CTT    2739
Cys Ala Ser Asn Val Ile Pro Pro Lys Glu Asp Pro Tyr Ala Gly Leu
            895                 900                 905

AGG TTT TGG AGC ATA GAC TTA AAA GAA AAG CTG TCT TTG GAC TTA GAC    2787
Arg Phe Trp Ser Ile Asp Leu Lys Glu Lys Leu Ser Leu Asp Leu Asp
        910                 915                 920
```

```
CAA TTT CCC TTG GGA AGA AGA TTC TTA GCT CAG CAA GGG GCA GGA TGT    2835
Gln Phe Pro Leu Gly Arg Arg Phe Leu Ala Gln Gln Gly Ala Gly Cys
925                 930                 935                 940

TCA ACT GTG AGA AAG AGA GCT GTT GCA ACC AGA AAT TCC AGT AAG CCT    2883
Ser Thr Val Arg Lys Arg Ala Val Ala Thr Arg Asn Ser Ser Lys Pro
            945                 950                 955

GCA AAA AGA AAA AAA ATC AAA GCT TAA                                 2910
Ala Lys Arg Lys Lys Ile Lys Ala
            960
```

(2) INFORMATION FOR SEQ ID NO:2:

(i) SEQUENCE CHARACTERISTICS:
        (A) LENGTH: 964 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Ser Ala Arg Lys Arg Val Lys Arg Ala Asn Val Tyr Asp Leu Tyr
1               5                   10                  15

Arg Thr Cys Lys Gln Ala Gly Thr Cys Pro Pro Asp Val Ile Pro Lys
                20                  25                  30

Val Glu Gly Asp Thr Ile Ala Asp Lys Ile Leu Lys Leu Gly Gly Leu
            35                  40                  45

Ala Ile Tyr Leu Gly Gly Leu Ala Ile Gly Thr Trp Ser Thr Gly Arg
        50                  55                  60

Val Ala Ala Gly Gly Ser Pro Arg Tyr Val Pro Leu Arg Thr Ser Gly
65                  70                  75                  80

Ser Thr Thr Ser Leu Ala Ser Val Gly Ser Arg Ala Gly Ala Ala Thr
                85                  90                  95

Gly Thr Arg Ser Ser Ile Thr Gly Ile Pro Leu Asp Thr Leu Glu Thr
                100                 105                 110

Ile Gly Ala Leu Arg Pro Gly Ala Tyr Glu Asp Thr Val Leu Pro Glu
            115                 120                 125

Ala Pro Ala Ile Val Thr Pro Asp Ala Val Pro Ala Asp Thr Gly Ile
        130                 135                 140

Asp Gly Leu Ser Ile Gly Thr Asp Ser Ser Thr Glu Thr Leu Ile Thr
145                 150                 155                 160

Leu Leu Glu Pro Glu Gly Pro Glu Asp Val Ala Val Leu Glu Leu Gln
                165                 170                 175

Pro Leu Asp His Ala Asn Trp Gln Val Ser Asn Ala Val His Gln Gly
            180                 185                 190

Ser Ala Tyr His Ala Pro Leu Gln Leu Gln Ser Ser Ile Ala Glu Thr
        195                 200                 205

Ser Gly Leu Glu Asn Ile Phe Val Gly Gly Ala Gly Leu Gly Asp Thr
    210                 215                 220

Gly Gly Glu Asn Ile Glu Leu Thr Phe Phe Gly Ser Pro Arg Thr Ser
225                 230                 235                 240

Thr Pro Arg Asn Leu Pro Gln Thr Ala Arg Gly Ile Leu Asn Trp Phe
                245                 250                 255

Ser Lys Arg Tyr Tyr Thr Gln Ile Pro Thr Glu Asp Pro Asp Val Phe
            260                 265                 270

Ser Ser Gln Thr Phe Ser Asn Pro Val Tyr Asp Pro Glu Pro Ala Val
        275                 280                 285

Leu Lys Gly Pro Ser Gly Arg Val Gly Leu Ser Gln Val Tyr Arg Pro
```

```
            290                 295                 300
Asp Tyr Ile Glu Thr Arg Gly Gly Gln Val Gly Pro Gln Leu His
305                 310                 315                 320
Val Arg Tyr Ser Leu Ser Thr Ile Thr Glu Asp Val Glu Ala Ile Pro
                325                 330                 335
Ile Ala Val Asp Glu Asp Thr Gln Gly Leu Ala Phe Leu Pro Leu His
                340                 345                 350
Glu Glu Pro Gly Asp Phe Glu Glu Ile Glu Leu Asp Asp Leu Gly Glu
                355                 360                 365
Glu His Ala Leu Leu Pro Lys Ser Ser Thr Ala Pro Ile Gly Ser Gly
        370                 375                 380
Val Arg Arg Ala Leu Ile Pro Gly Gln Gly Phe Ser Ala Thr Arg Pro
385                 390                 395                 400
Thr Gly Val Val Thr Tyr Gly Ser Pro Asp Met Tyr Pro Ala Ser Pro
                405                 410                 415
Val Gly Pro Asp Ser Thr Ser Pro Ser Leu Val Ile Asp Asp Asn Thr
                420                 425                 430
Thr Thr Pro Ile Ile Ile Ile Asp Gly His Thr Val Asp Leu Tyr Ser
                435                 440                 445
Asn Asn Tyr Ser Leu His Pro Ser Leu Leu Arg Lys Arg Lys Lys Arg
450                 455                 460
Lys His Ala Met Ala Leu Trp Gln Gln Gly Gln Lys Leu Tyr Leu Pro
465                 470                 475                 480
Pro Thr Pro Val Ser Lys Val Leu Cys Ser Glu Thr Tyr Val Gln Arg
                485                 490                 495
Lys Ser Ile Phe Tyr His Ala Glu Thr Glu Arg Leu Leu Thr Val Gly
                500                 505                 510
His Pro Tyr Tyr Gln Val Thr Val Gly Asp Lys Thr Val Pro Lys Val
                515                 520                 525
Ser Ala Asn Gln Phe Arg Val Phe Lys Ile Gln Leu Pro Asp Pro Asn
        530                 535                 540
Gln Phe Ala Leu Pro Asp Arg Thr Val His Asn Pro Ser Lys Glu Arg
545                 550                 555                 560
Leu Val Trp Ala Val Ile Gly Val Gln Val Ser Arg Gly Gln Pro Leu
                565                 570                 575
Gly Gly Thr Val Thr Gly His Pro Thr Phe Asn Ala Leu Leu Asp Ala
                580                 585                 590
Glu Asn Val Asn Arg Lys Val Thr Ala Gln Thr Thr Asp Asp Arg Lys
                595                 600                 605
Gln Thr Gly Leu Asp Ala Lys Gln Gln Gln Ile Leu Leu Leu Gly Cys
        610                 615                 620
Thr Pro Ala Glu Gly Glu Tyr Trp Thr Thr Ala Arg Pro Cys Val Thr
625                 630                 635                 640
Asp Arg Ile Glu Asn Val Ala Cys Pro Pro Leu Glu Leu Lys Asn Lys
                645                 650                 655
His Ile Glu Asp Gly Asp Met Met Glu Ile Gly Phe Gly Ala Ala Asp
                660                 665                 670
Phe Lys Thr Leu Asn Ala Ser Lys Ser Asp Leu Pro Phe Asp Ile Gln
                675                 680                 685
Asn Glu Ile Cys Leu Tyr Pro Asp Tyr Leu Lys Met Ala Glu Asp Ala
                690                 695                 700
Ala Gly Asn Ser Met Phe Phe Ala Arg Lys Glu Gln Val Tyr Val
705                 710                 715                 720
```

-continued

```
Arg His Ile Trp Thr Arg Gly Gly Ser Glu Lys Glu Ala Pro Ser Lys
                725                 730             735

Asp Phe Tyr Leu Lys Asn Gly Arg Gly Glu Glu Thr Leu Lys Ile Pro
            740             745                 750

Ser Val His Phe Gly Ser Pro Ser Gly Ser Leu Val Ser Thr Asp Asn
        755             760             765

Gln Ile Phe Asn Arg Pro Tyr Trp Leu Phe Arg Ala Gln Gly Met Asn
    770             775             780

Asn Gly Ile Ala Trp Asp Asn Leu Leu Phe Leu Thr Val Gly Asp Asn
785             790             795                         800

Thr Arg Gly Thr Asn Leu Ser Ile Ser Val Ala Ala Asp Gly Asn Ala
                805             810                     815

Leu Ser Glu Tyr Asp Thr Gly Lys Phe Asn Leu Tyr His Arg His Met
                820             825             830

Glu Glu Tyr Lys Leu Ala Phe Ile Leu Glu Leu Val Ser Val Glu Ile
            835             840             845

Thr Ala Gln Thr Val Ser His Leu Gln Gly Leu Met Pro Ser Val Leu
    850             855             860

Gln Asn Trp Glu Ile Gly Val Gln Pro Pro Ala Ser Ser Ile Leu Glu
865             870             875                         880

Asp Thr Tyr Arg Tyr Ile Glu Ser Pro Ala Thr Lys Cys Ala Ser Asn
                885             890             895

Val Ile Pro Pro Lys Glu Asp Pro Tyr Ala Gly Leu Arg Phe Trp Ser
            900             905             910

Ile Asp Leu Lys Glu Lys Leu Ser Leu Asp Leu Asp Gln Phe Pro Leu
            915             920             925

Gly Arg Arg Phe Leu Ala Gln Gln Gly Ala Gly Cys Ser Thr Val Arg
    930             935             940

Lys Arg Ala Val Ala Thr Arg Asn Ser Ser Lys Pro Ala Lys Arg Lys
945             950             955                         960

Lys Ile Lys Ala
```

METHOD OF TREATMENT USING PAPILLOMAVIRUS L2 PROTEIN

This application is a continuation under 35 U.S.C. §120 of U.S. patent application Ser. No. 08/170,185, filed Apr. 24, 1994, now abandoned, which claims priority under §365(c) from 371 PCT Application Serial No. PCT/GB92/01902, filed Jun. 17, 1992, which claims priority from Great Britain Patent Application No. 9113809.9, filed Jun. 26, 1991.

FIELD OF THE INVENTION

The present invention relates to the use of papillomavirus L2 protein in medicine, particularly for the regression of papillomavirus tumors in mammals; and to pharmaceutical formulations comprising the L2 protein.

BACKGROUND OF THE INVENTION

Papillomaviruses induce a variety of lesions both in humans and in animals. Some papillomas, albeit benign, are themselves a clinical problem, such as laryngeal papillomas of children (Steinberg and Abramson, 1985) or penile papillomas of bulls (Jarrett, 1985a), and others are known to be a risk factor in the pathogenesis of cancer, as in the case of flat lesions of the cervix or penile condylomata in humans (zur Hausen, 1978). Therefore both in human and veterinary medicine an antiviral vaccine, particularly a therapeutic one inducing lesion rejection, would be of major importance. Vaccination studies in humans present several problems: first of all experimentation is ethically unacceptable and, secondly, very limited amounts of virus are available as some lesions, in particular those of the cervix, do not produce viral progeny, and no in vitro system is yet available which allows vegetative replication of virus. The production of viral proteins in bacteria and the use of synthetic peptides have circumvented this last problem and have allowed the ongoing analysis of the immune response to papillomavirus infection (see for instance Jenison et al, 1988: Jochmus-Kudielka et al, 1989; Tindle et al, 1990, Dillner, 1990 and Strang et al, 1990). Whilst investigation into the feasibility of a human papillomavirus vaccine is still at an early stage, effective prophylactic vaccines, both natural (Jarrett et al, 1990a) and genetically engineered (Pilachinski et al, 1986) have already been produced against bovine papillomaviruses, and regression of Shope papillomas has been achieved by vaccinating rabbits with tumour tissue extracts (Evans et al, 1962). The bovine system is an excellent model for the human one, given the several similarities between the two: multiple virus types with high lesion specificity (Campo et al, 1981; Jarrett et al, 1984), homology of genetic structure (Danos et al, 1984) and progression of some lesions to malignancy (Jarrett et al, 1978). The bovine system also presents several advantages: cofactors in oncogenesis are known (Jarrett et al, 1978; Campo and Jarrett, 1986) and, above all, direct experimentation is possible (Jarrett, 1985a).

It has recently been shown that vaccination with bovine papillomavirus type 2 (BPV-2) successfully prevented infection by the same virus (Jarrett et al, 1990a), but not by other virus types (Jarrett et al, 1990b). Prevention was accompanied by production of neutralising antibodies in the serum of vaccinated animals, indicating that neutralising epitopes are present in the virus.

SUMMARY OF THE INVENTION

Generally speaking, the present invention resides in the discovery that the papillomavirus L2 protein is therapeutically effective in the treatment of papillomavirus tumors or lesions.

Thus, the present invention provides the use of papillomavirus L2 protein in medicine, particularly for therapy of papillomavirus tumors or lesions.

The invention also provides a pharmaceutical formulation for the therapy of papillomavirus tumors or lesions, which comprise papillomavirus L2 protein in admixture with a pharmaceutically acceptable carrier.

The invention further provides papillomavirus L2 protein for use in the production of a medicament for use in medicine, particularly for use in the therapy of papillomavirus tumors or lesions.

The invention still further provides a method of treating a mammal for the therapy of papillomavirus tumors or lesions, which comprise the administration of papillomavirus L2 protein to the mammal.

Generally speaking, the therapeutic effect of the L2 protein may be limited to the respective papillomavirus type. Thus, for general therapeutic applications, especially where the particular papillomavirus type is unknown, it may be desirable to employ a mixture of L2 proteins from a variety of papillomavirus types.

Generally, the therapy will be applicable to papillomavirus infections of mammals, including humans and animals. In humans, the invention is particularly applicable for the therapy and regression of laryngeal tumors, skin cancer tumors and genital lesions, whether malignant or not. In animals, the therapy is particularly useful for the regression of tumors on animals, for example the removal of warts from the udders of milk cows, or removal of papillomas of the alimentary canal and for the treatment of horses and donkeys. Prophylactic vaccination may also be employed.

The L2 protein is generally produced by recombinant DNA techniques. In particular, a plasmid containing the gene coding for the L2 protein may be transfected into *E. coli* and cultured. The entire L2 protein as it exists in nature may be employed, or a fragment (such as amino acid 90 to 467 of BPV-2 as disclosed hereafter) or fragments thereof may be used providing that the therapeutic effectiveness is retained. The L2 protein may be the native form, with additions, deletions or substitutions which do not substantially effect its therapeutic effectiveness.

The L2 protein will usually be administered in the form of a pharmaceutical formulation. The formulation contains a pharmaceutically acceptable carrier. The carrier must be acceptable in the sense of being compatible with the other ingredients of the formulation and not deleterious to the recipient thereof.

Since the protein is broken down in the stomach, oral administration is not preferred. The pharmaceutical formulation is preferably formulated for parenteral administration, including subcutaneous, intramuscular and intravenous injection; or as a suppository or pessary. For parenteral administration the formulation may be presented as a sterile solution or suspension in a suitable liquid vehicle, which may also contain preservatives and materials for rendering the formulation isotonic. The formulations may be presented in unit-dose or multi-dose containers. The carrier will generally be apyrogenic. Each dose will generally contain 100 to 10,000 micro grams of the L2 protein.

In order to enhance the therapeutic effect of the protein, it may be administered together with an adjuvant, such as Freund's incomplete adjuvant, as an oil-in-water emulsion or using other adjuvant systems known in the art such as L101 and DDA as used in Pilacinski et al. (1986).

DESCRIPTION OF PREFERRED EMBODIMENTS

Embodiments of the present invention will now be described by way of example only with reference to the following experimental protocol.

EXAMPLE 1

(BPV-2 Virus)

Figure 1:
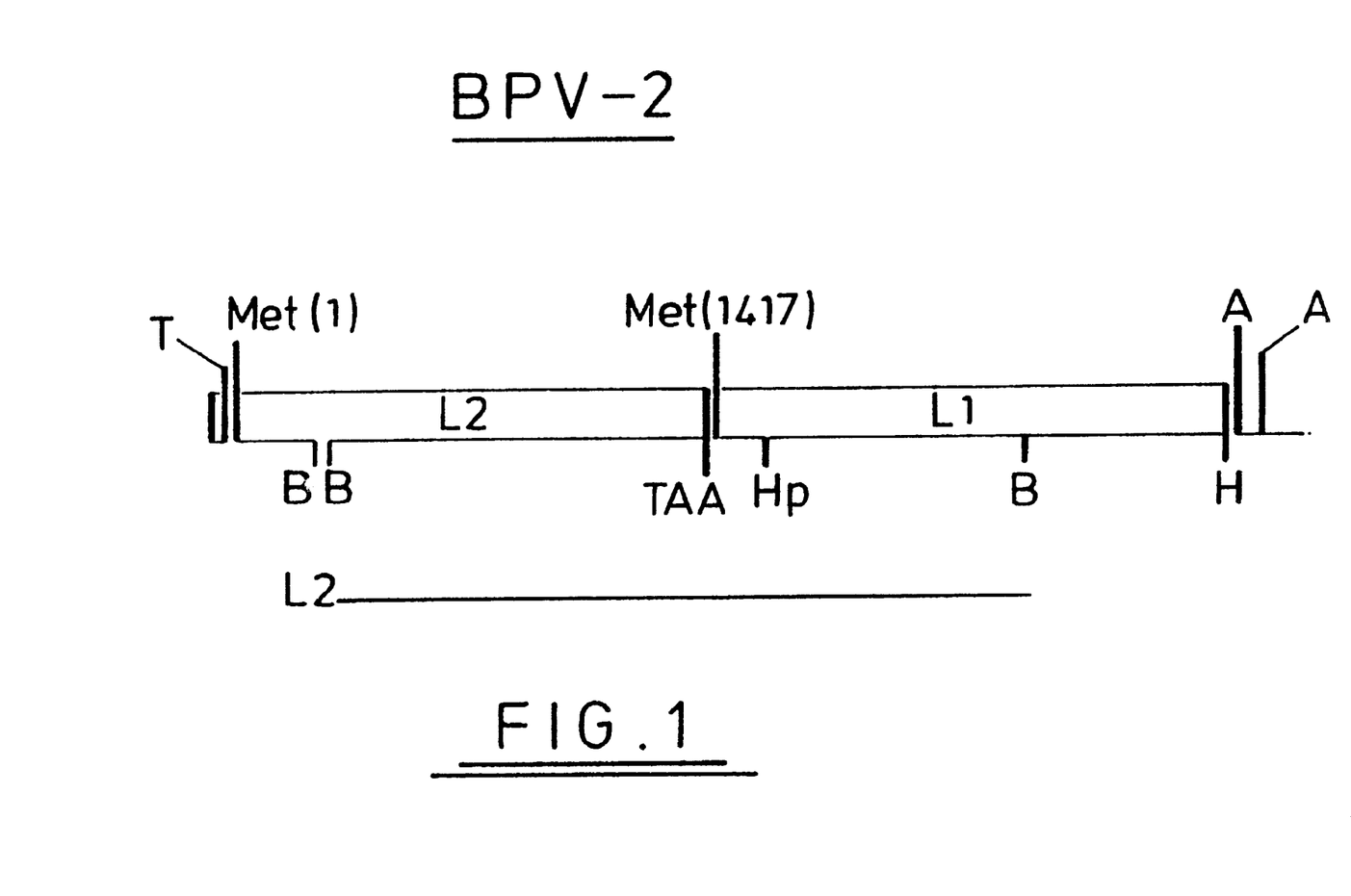
FIG. 1 shows the open reading frames for L2 protein of BPV-2.

FIG. 1 referred to in the experimental protocol shows the L1 and L2 open reading frames (ORF's) of BPV2 and the restriction enzyme sites used for cloning.

T=TATA box; A=polyadenylation site; Met=translation initiation codon; TAA=translational termination codon; B=BamHI site; Hp=HpaI site; H=HindIII site. The DNA fragment cloned in pUR is indicated as L2 (BamHI-BamHI). The nucleotide numbering of Potter and Meinke (1985) is used.

Materials and Methods

Calves

Twenty one 12-week old male Friesian calves were obtained from a papilloma-free source. They were randomly assigned to three initial groups, which were housed in separate, clean, well ventilated pens in the isolation unit of the Department of Veterinary Pathology, Glasgow. All the calves were bled on arrival for haematological analysis and to obtain pre-inoculation serum samples. The experiment was started when the calves were 16 weeks old.

Production of L2 Peptide of BPV-2 in *Escherichia coli*

The open reading frame (ORF) encoding the L2 peptide was isolated by digesting the BPV-2 genome cloned in pAT 153 (Campo and Coggins, 1982) with Bam HI. This produced one fragment of 2030 bp (nt 268–2298) numbered according to the nucleotide (nt) sequence of Potter and Meinke (1985), where nt 1 is the A of the ATG codon of the L2 ORF (FIG. 1); this fragment contains the majority of the L2 ORF (from aa 90 to aa 467, L2), the L2 ORF stop codon and the 5' half of the L1 ORF, which would not be expressed because of the termination codon. The fragment was cloned in the pUR vector series (Ruther and Muller-Hill, 1983), giving rise to pL2, and transfected into *E. Coli* JM 109. Peptide for vaccination was prepared from mid-log phase cultures induced for 4 hours in L-broth supplemented with 100 ug/ml ampicillin and containing 1 mM IPTG. Bacterial pellets resuspended in lysozyme buffer (50 mM TRIS-HCl pH 8.0, 10 mM McCl$_2$, 50 mM glucose, 1 mg/ml lysozyme) were left at 20° C. for 10 min, when EDTA was added to 50 mM. Following cell lysis by the addition of Triton X100 to 1% (v/v), the fusion peptide was pelleted at 39000 g for 30 min and resuspended by boiling and sonication in 5% SDS, 50 mM B-mercaptoethanol, 50 mM TRIS-HCl, pH 8.0 Purity of 90–95% was achieved by preparative SDS PAGE, the final yields being up to 2 mg of product per gm wet weight of cells. The protein was stored at −20° C. before use, but prolonged storage caused degradation.

Experimental Design

The vaccination experiments were designed as follows: In group A, six animals were vaccinated prophylactically with the gel-purified L2 (one calf had to be withdrawn from the experiment because of pneumonia); three of these animals were also vaccinated therapeutically with the gel-purified L2 nine weeks after callenge. In group B, eleven animals received no prophylactic vaccination; after tumour formation three of these animals were therapeutically vaccinated with gel-purified L2, while eight animals received no vaccine at all and were therefore used as controls.

Vaccination

The calves receiving the L2 vaccine were given a 1 ml PBS suspension containing 650 ug of the L2 fusion protein plus 1 ml of Freund's incomplete adjuvant (FIA) into the right quadriceps muscle. This was repeated fourteen days later as a boost, but with only 500 ug of protein.

Virus Challenge

BPV-2 was purified from a skin fibropapilloma (Campo et al, 1981) and the concentration of viral particles was estimated by the electron microscope assay (Jarrett et al, 1990a). Each calf was challenged at multiple sites with $10^{12}$ virus particles as described by Jarrett and other (1990a) either four weeks after vaccination (two weeks after the boost) or nine weeks before vaccination.

Biopsies

Biopsies were performed as described by Jarrett et al (1990a). Immunocytochemical studies were made by the peroxidase-anti-peroxidase (Hsu et al, 1981) or immunogold (Holgate et al, 1983) techniques using rabbit anti-BPV-2 serum as described by Jarrett et al (1984).

Virus Neutralization Assay

The presence of neutralizing antibodies in serum samples was determined by the cell transformation inhibition assay described previously (Jarrett et al, 1990a). This assay takes advantage of the ability of BPV-2 to transform primary bovine fibroblasts in vitro (Jarrett, 1985b), which is abrogated by pre-incubation of virus with immune serum.

Results

Characterization of Fusion Protein

The size of the BPV-2 B-gal-L2 fusion protein was estimated on PAGE to be 180 kDa well in agreement with the predicted size of 156 kDa.

The L2 fusion protein was characterized immunologically. It was injected into rabbits or calves and the antisera were tested against the fusion protein itself and against virion proteins in both Ouchterlony and Western blots assays. The antisera were reactive with both the engineered protein (data not shown) and its viral L2 (62 kDA) counterpart. In reciprocal experiments, rabbit or calf antisera raised against SDS-disrupted virus were reactive with the fusion protein. Although N-terminus truncated, the fusion protein therefore shares epitopes with virus and presents them effectively to the host immune system.

Therapeutic Vaccination with BPV-2 L2 Fusion Protein

Five animals were vaccinated prophylactically; three of these and three unvaccinated animals were vaccinated therapeutically nine weeks after challenge. As the same results were obtained with the two groups of calves, they will be considered together. All animals developed fibropapillomas four weeks after challenge (Table 1). Six vaccinated animals were still bearing tumors at ten weeks. In the other two vaccinated calves the tumors were entering the rejection phase: the epithelium was virtually normal and the sub-epithelial tissue was mainly composed of hyalinised collagen. There was a drastic reduction in the number of fibroblasts and a massive infiltration of lymphocytes and macrophages in the sub-epithelial tissue. All vaccinated animals had reached that stage by week thirteen. By week sixteen the tumors had definitely regressed. There were small plaque-like lesions with hyperkeratosis, but virtually all the normal skin adnexal elements were present. Some lymphocytes and macrophages were still present. The control animals were still bearing virus-producing tumors (Table 1). Neutralizing antibodies appeared in the serum of the vaccinated calves at the same time and with the same titre as the control animals (data not shown). Serum antibodies to L2 were however detected soon after vaccination and before challenge (data not shown).

Vaccination with BPV-2 L2 Promotes Tumour Rejection.

Vaccination with the L2 fusion protein, whether delivered before or after challenge, induced early tumor regression. Tumor regression was accompanied by infiltration of the lesion by macrophages and lymphocytes, a process consistently observed when natural regression takes place (Jarrett, 1985a). Thus it appears that the L2 protein encodes epitopes specific for the cellular effector arm of the immune system. Zhou et al (1991) have recently shown that the L1 protein of HPV-16, when expressed in vaccinia virus, induces cytotoxic T-lymphocytes in infected mice, providing another example of T-cell activation by a structural protein.

In field and experimental cases, rejection takes place approximately twelve months after infection and it generally follows ulceration of the lesion. This is consistent with the L2 being internal to the virion (Jin et al, 1989) and therefore not readily exposed to the host immune system; ulceration of the tumor with associated bleeding would lead to the exposure of relatively large amounts of antigen to the immune cells. Anti L2 antibodies were present in the serum of the vaccinated animals, but these had no activity in the neutralization assay. Therefore, unless some neutralizing epitopes are present in the first N-terminus amino acids of L2, which are missing in our fusion protein, it is unlikely that L2 plays a significant role in conferring prophylactic protection.

TABLE 1

Effect of vaccination with BPV-2 L2 fusion proteins.

| | WEEKS POST CHALLENGE | | | | |
|---|---|---|---|---|---|
| | 4 | 7 | 10 | 13 | 16 |
| CONTROLS | | | | | |
| 1 | FP | FP | FP | nd | nd |
| 2 | FP | FP | FP | nd | nd |
| 3 | FP | FP | FP | nd | nd |
| 4 | FP | FP | FP | nd | nd |
| 5 | FP | FP | FP | nd | nd |
| 6 | FP | FP | FP | nd | nd |
| 7 | FP | nd | FP | FP | FP |
| 8 | FP | nd | FP | FP | FP |
| L2 VACCINATES (bc) | | | | | |
| 13* | FP | nd | FP | — | — |
| 14 | FP | nd | — | — | — |
| 15* | FP | nd | FP | — | — |
| 16 | FP | nd | — | — | — |
| 17* | FP | nd | FP | — | — |
| L2 VACCINATES (ac) | | | | | |
| 18 | FP | nd | FP | — | — |
| 19 | FP | nd | FP | — | — |
| 20 | FP | nd | FP | — | — |

FP-fibropapilloma; nd = not done; — = no tumors; bc = before challenge; ac = after challenge; animals marked* were vaccinated both before and after challenge.

EXAMPLE 2
(BPV-4 Virus)
Production of BPV-4 L2 Protein

L2 open reading frame (ORF) of BPV-4 was cloned following the general procedure of Example 1, except that plasmid pGEX was employed which resulted in a L2 fusion protein with glutathione S-transferase (GST) as coprotein. The L2 ORF was cloned as the whole ORF (encoding amino acids 8 to 525) and as the three fragments encoding amino acids 11–201, 203–329, and 330–525. In the subsequent vaccination experiments a mixture of these four was used. Expression was in *E.coli* and the proteins were purified by gel chromatography, as before.

The E7 protein was prepared in analogous manner.
Vaccination

Vaccination was carried out as in Example 1 using Freund's Incomplete Adjuvant, except that doses of 1 mg total protein (L2 and fragments) was administered both as the dose (day 0) and the booster (day 28).

Figure 2:
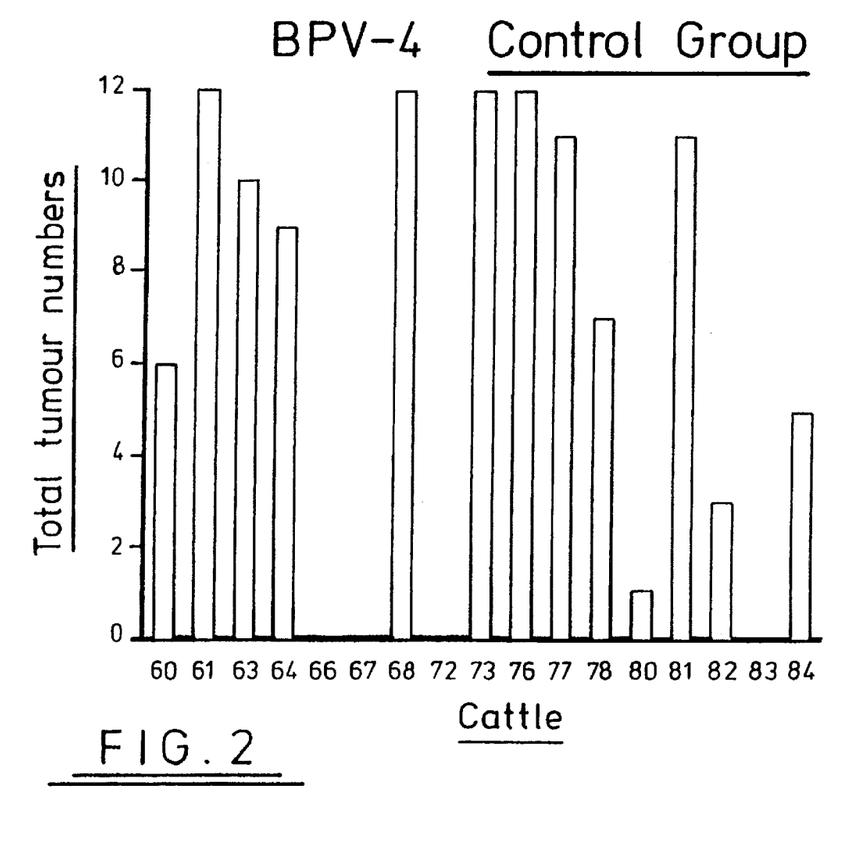
FIGS. 2, 3 and 4 show the results of vaccination experiments using L2 protein of BPV-4 for control group, L2 vaccinated group, and L2 plus E7 vaccinated group respectively.
Figure 3:
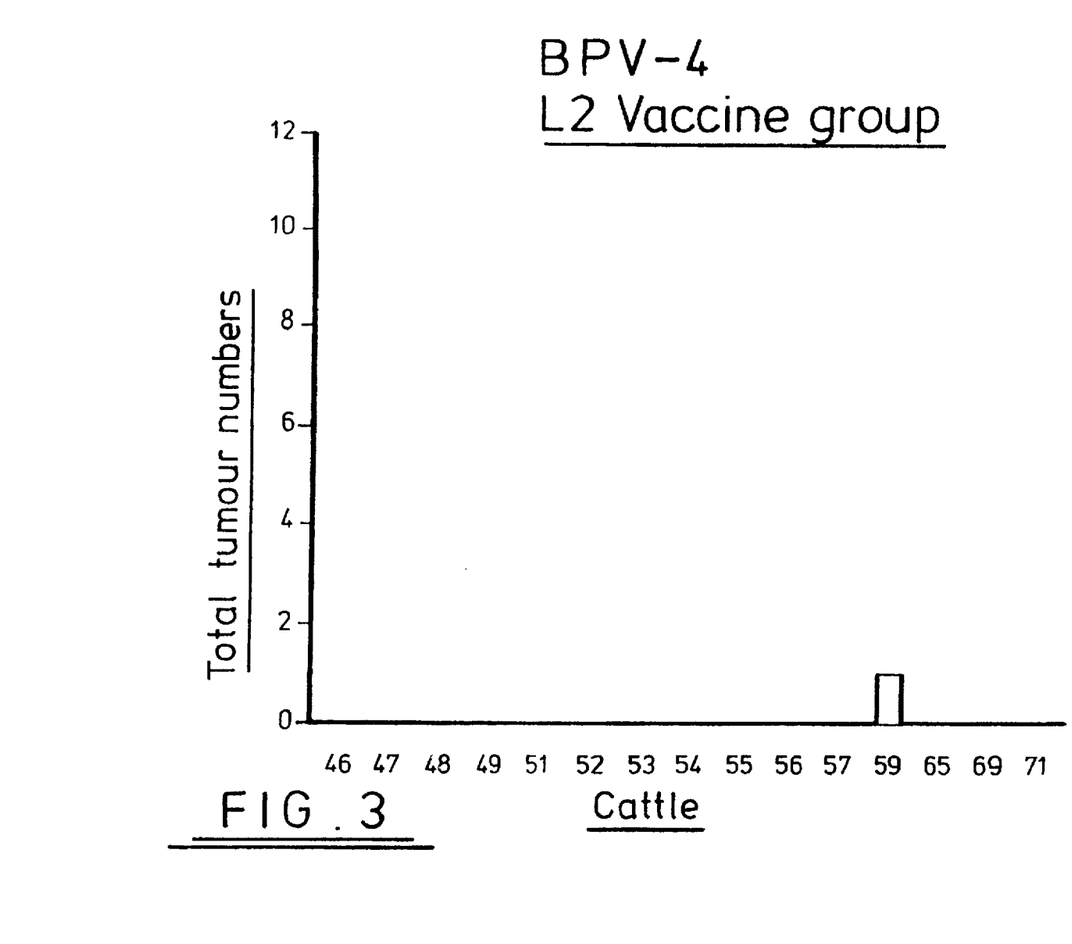
Figure 4:
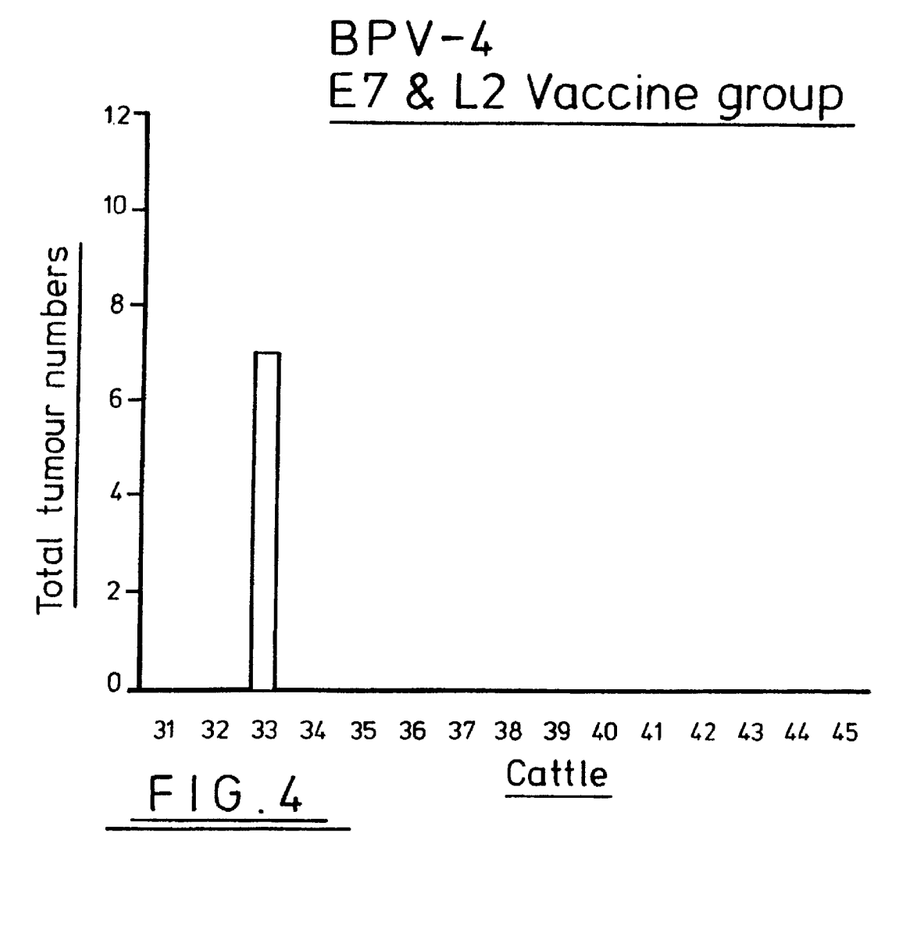

47 calves, of about 10 weeks of age at the start of the experiment, were housed in an isolation compound. They were divided into 2 groups of 15 and one of 17 (controls). Group 1 was vaccinated with L2 vaccine alone. Group 2 was vaccinated with L2 plus E7 vaccine. Group 3 was the control non-vaccinated group. All animals were examined and bled before Day 0. They were vaccinated on Day 0 and Day 28. They were challenged with BPV-4 virus on Day 43 and examined for tumor formation 4 and 7 weeks later.
Results The results are shown in FIG. 2 (controls), FIG. 3 (L2 alone) and FIG. 3 (L2 plus E7). The controls showed a good tumor response, 13 of the 17 animals being infected. In the L2 vaccinated group only one animal showed a response (a small plaque). In the group vaccinated with L2 plus E7 only one animal developed tumors.

Thus the L2 protein of BPV-4 appears to be exerting a strong prophylactic effect in preventing tumor formation (in contrast to BPV-2 where a therapeutic effect was exhibited).

REFERENCES

Campo M S and Coggins L W (1982) Molecular cloning of bovine papillomavirus genomes and comparison of their sequence homologies by heteroduplex mapping. Journal General Virology, 63, 255–264.

Campo M S and Jarrett W F H (1986) Papillomavirus infection in cattle: viral and chemical cofactors in naturally occurring and experimentally induced tumors. Ciba Foundation Symposium 120; Papillomaviruses. pp117–131.

Campo M S, Moar M H, Laird H M and Jarrett W F H (1981) Molecular heterogeneity and lesion site specificity of cutaneous bovine papillomaviruses. Virology, 113, 323–335.

Cowsert L M, Lake P and A B Jenson (1987) Topographical and conformational epitopes of bovine papillomavirus type 1 defined by monoclonal antibodies. Journal of the National Cancer Institute, 79, 1053–1057.

Danos 0, Giri I, Thierry F and Yaniv M (1984) Papillomavirus Genomes: Sequences and Consequences. The Journal of Investigative Dermatology, 83, 7s–11s.

Dillner J (1990) Mapping of linear epitopes of human papillomavirus type 16: the E1, E2, E4, E5, E6 and E7 open reading frames. International Journal of Cancer, 46, 703–711.

Dvoretzky I, Shober R, Chattopadhyay S K and Lowy D R (1980) A quantitative in vitro focus forming assay for bovine papillomavirus. Virology, 103, 369–375.

Evans C A, Gorman L R, Ito Y and Weiser R S (1962) Antitumour immunity in the Shope papilloma-carcinoma complex of rabbits. I.Papilloma regression induced by homologous and autologous tissue vaccines. Journal of the National Cancer Institute, 29, 277–285.

Holgate C S, Jackson P, Cowen P N and Berol C C (1983) Immunogold silver staining: a new method of immunostaining with enhanced sensitivity. Journal of histochemistry and cytochemistry, 31, 938–944.

Hsu S M, Raine L and Fanger H (1981) Use of avidin-biotin-peroxidase complex (ABC) in immunoperoxidase techniques. Journal of histochemistry and cytochemistry, 29, 577–580.

Jaqqar R T, Pennie W D, Smith K T, Jackson M E and Campo M S (1990) Cooperation between bovine papillomavirus type 4 and ras in the morphological transformation of primary bovine fibroblasts. Journal of General Virology, 71, 3041–3046.

Jarrett W F H (1985a) The natural history of bovine papillomavirus infection. Advances in viral oncology. Ed: G. Klein. vol 5, pp83–102.

Jarrett W F H (1985b) Biological characteristics of bovine papillomaviruses. UCLA Symposium. Ed P M Howley and T R Broker. vol 32: Papillomaviruses; Molecular and clinical aspects. pp299–303.

Jarrett W F H, McNeil P E, Grimshaw W T R, Selman I E and McIntyre W I M (1978) High incidence area of cattle cancer with a possible interaction between an environmental carcinogen and a papillomavirus. Nature, 274, 215–217.

Jarrett W F H, Campo M S, O'Neil B W, Laird H M and Coggins L W (1984) A novel bovine papillomavirus (BPV-6) causing true epithelial papillomas of the mammary gland skin: a member of a proposed new subgroup. Virology, 136, 255–264.

Jarrett W F H, O'Neil B W, Gaukroger J M, Laird H M, Smith K T and Campo M S (1990a) Studies on vaccination against papillomaviruses: a comparison of purified virus, tumor extract and transformed cells in prophylactic vaccination. The Veterinary Record, 126, 449–452.

Jarrett W F H, O'Neil B W, Gaukroger J M, Smith K T, Laird H M and Campo M S (1990b) Studies on vaccination against papillomaviruses:the immunity after infection and vaccination with bovine papillomaviruses of different types. The veterinary Record, 126, 473–475.

Jenison S A, Firzlaff J M, Langenberg A and Galloway D A (1988) Identification of immunoreactive antigens of human papillomavirus type 6b by using *Escherichia coli*-expressed fusion proteins. Journal of Virology, 62, 2115–2123.

Jin X W, Cowsert L M, Pilacinski W P and Jenson A B (1989) Identification of L2 open reading frame gene products of bovine papillomavirus type 1 using monoclonal antibodies. Journal of General Virology, 70, 1133–1140.

Jin X W, Cowsert L M, Marshall D, Reed D, Pilacinski W P, Lim L and Jenson A B (1990) Bovine serological response to a recombinant BPV-1 major capsid protein vaccine. Intervirology, 31, 345–354.

Jochmus-Kudielka I, Schneider A, Braun R, Kimmig R, Koldovsky U, Schneweis K E, Seerdof K and Gissmann L (1989) Journal of the National Cancer Institute, 81, 1698–1704.

Kreider J A, Howett M K, Wolfe S A, Bartlett G L, Zaino R J, Sedlacek T V and Mortel R (1985) Morphological transformation in vivo of human uterine cervix with papillomavirus from condylomata acuminata. Nature, 317, 639–640.

Meneguzzi M, Cerni C, Kieny M P Lathe R (1991) Immunization against Human Papillomavirus type 16 tumuor cells with recombinant vaccinia viruses expressing E6 and E7. Virology, 181, 62–69.

Pilacinski W P, Glassman D L, Glassman K F, Reed D E, Lum M A, Marshall R F, Muscoplat C C and Faras A J (1986) Immunization against bovine papillomavirus infection. Ciba foundation Symposium 120; Papillomaviruses. pp136–148.

Potter H L and Meinke W J (1985) Nucleotide sequence of bovine papillomavirus type 2 late region. Journal General Virology, 66, 187–193.

Ruther U and Muller-Hill B (1983) Easy identification of CDNA clones. EMBO Journal, 2, 1791–1794.

Steinberg B M and Abramson A L (1985) Laryngeal papillomas. Clinics in Dermatology, 3, 130–138.

Strand G, Hickling J K, McIndoe G A J, Howland K, Wilkinson D, Ikeda H and Rothbard J B. (1990) Human T-cell responses to human papillomavirus type 16 L1 and E6 synthetic peptides: identification of T-cell determinants, HLA-DR restriction and virus type specificity. Journal General Virology, 71, 423–431.

Tindle R W, Smith J A, Geysen H m, Selvey L A and Frazer I H (1990) Identification of B epitopes in human papillomavirus type 16 E7 open reading frame protein. Journal General Virology, 71, 1347–1354.

Zhou J. McIndoe A, Davies H, Sun X-Y and Crawford L (1991) The induction of cytotoxic T-lymphocyte precursor cells by recombinantvaccinia virus expressing human papillomavirus type 16 L1. Virology, 181, 203–210.

zur Hausen H (1976) Condyloma acuminata and human genital cancer. Cancer Research, 36, 794.

---

We claim:

1. A method of therapeutically treating a papillomavirus tumor or lesion, said method comprising administering to a subject infected with a papillomavirus a therapeutically effective dosage of a medicament comprising papillomavirus L2 protein, or a therapeutically effective fragment thereof, wherein said therapeutically effective fragment comprises a peptide of at least about 127 amino acids of said papillomavirus L2 protein, or a mixture of therapeutically effective fragments of papillomavirus L2 protein, wherein each of said fragments comprises at least about 127 amino acids of said papillomavirus L2 protein.

2. The method according to claim 1, wherein the papillomavirus L2 protein or therapeutically effective fragment thereof is present in the form of a fusion protein with a different co-protein.

3. The method according to claim 2, wherein the co-protein in said fusion protein is beta-galactosidase.

4. The method according to claim 1, wherein the L2 protein is a bovine papillomavirus BPV-2 protein.

5. The method according to claim 4, wherein the L2 protein fragment comprises substantially amino acids 90 to 467 of SEQ ID NO:2.

6. The method according to claim 1, wherein the papillomavirus L2 protein or therapeutically effective fragment thereof is produced by recombinant DNA techniques.

7. The method according to claim 1, wherein the medicament is in the form of an injectable formulation.

8. The method according to claim 7, wherein the medicament further comprises an adjuvant.

9. A method of treating a mammal for the therapy of papillomavirus tumors or lesions which comprises the administration of papillomavirus L2 protein or therapeutically effective fragment thereof to the mammal in a therapeutically effective dosage, wherein said therapeutically effective fragment comprises a peptide of at least about 127 amino acids from said papillomavirus L2 protein.

10. The method according to claim 4, wherein said therapeutically effective fragment comprises amino acids 11 to 201 of SEQ ID NO:2.

11. The method according to claim 4, wherein said therapeutically effective fragment comprises amino acids 203 to 329 of SEQ ID NO:2.

12. The method according to claim 4, wherein said therapeutically effective fragment comprises amino acids 330 to 525 of SEQ ID NO:2.

13. The method according to claim 1, wherein the L2 protein is a bovine papillomavirus protein.

* * * * *